US010192726B1

(12) United States Patent
Wiederin et al.

(10) Patent No.: US 10,192,726 B1
(45) Date of Patent: Jan. 29, 2019

(54) RAPID INLINE PREPARATION OF A DILUTED SAMPLE

(71) Applicant: Elemental Scientific, Inc., Omaha, NE (US)

(72) Inventors: Daniel R. Wiederin, Omaha, NE (US); Kyle W. Uhlmeyer, Omaha, NE (US); Austin Schultz, Omaha, NE (US); Jonathan Hein, Bennington, NE (US)

(73) Assignee: ELEMENTAL SCIENTIFIC, INC., Omaha, NE (US)

( * ) Notice: Subject to any disclaimer, the term of this patent is extended or adjusted under 35 U.S.C. 154(b) by 0 days.

(21) Appl. No.: 14/518,043

(22) Filed: Oct. 20, 2014

Related U.S. Application Data (60) Provisional application No. 61/892,570, filed on Oct. 18, 2013, provisional application No. 61/971,857, filed on Mar. 28, 2014.

(51) Int. Cl.
*G01N 1/38* (2006.01)
*H01J 49/04* (2006.01)
*H01J 49/00* (2006.01)

(52) U.S. Cl.
CPC ........... *H01J 49/0454* (2013.01); *G01N 1/38* (2013.01); *H01J 49/0031* (2013.01); *G01N 2001/383* (2013.01)

(58) Field of Classification Search
CPC ............... G01N 2001/383; G01N 1/38; H01J 49/0031; H01J 49/0454
USPC ............................................. 73/61.59, 61.41
See application file for complete search history.

(56) References Cited

U.S. PATENT DOCUMENTS

| | | | | |
|---|---|---|---|---|
| 6,166,379 A | * | 12/2000 | Montaser | G01N 21/714 219/121.5 |
| 8,650,936 B2 | * | 2/2014 | Lee et al. | 73/61.56 |
| 8,925,375 B1 | * | 1/2015 | Wiederin | H01J 49/04 73/61.55 |
| 8,944,102 B1 | * | 2/2015 | Wiederin | F16K 11/0743 137/625.46 |
| 9,177,772 B1 | * | 11/2015 | Wiederin | H01J 49/105 |
| 9,239,581 B1 | * | 1/2016 | Wiederin | G05D 11/02 |
| 2012/0262178 A1 | * | 10/2012 | Dourdeville | G01N 24/08 324/321 |
| 2013/0014568 A1 | * | 1/2013 | Lee | G01N 30/10 73/61.56 |
| 2014/0014585 A1 | * | 1/2014 | Dourdeville | G01N 30/04 210/656 |

\* cited by examiner

*Primary Examiner* — Manish S Shah
*Assistant Examiner* — Suman K Nath
(74) *Attorney, Agent, or Firm* — Kevin E. West; Advent, LLP (57) ABSTRACT

A sample introduction system providing variable online dilution of a sample is described. In one or more implementations, a device includes a spectrometry analysis system that employs example techniques in accordance with the present disclosure includes an inline dilution environment, including a first valve assembly configured to prepare a sample by accepting at least one of the sample, a diluent, a carrier, or an internal standard, where the first valve assembly includes a first sample loop; and a second valve assembly configured to prepare the sample by accepting the sample from the first valve assembly, where the second valve assembly is coupled to the first valve assembly, and where the second valve assembly includes a second sample loop.

18 Claims, 7 Drawing Sheets

RAPID INLINE PREPARATION OF A DILUTED SAMPLE

CROSS-REFERENCE TO RELATED APPLICATIONS

The present application claims the benefit under 35 U.S.C. § 119(e) of U.S. Provisional Application Ser. No. 61/892,570, filed Oct. 18, 2013, and titled "RAPID INLINE PREPARATION OF A DILUTED SAMPLE," and of U.S. Provisional Application Ser. No. 61/971,857, filed Mar. 28, 2014, and titled "TIME BASED DILUTION OF SAMPLES PRIOR TO ANALYSIS," which is herein incorporated by reference in its entirety.

BACKGROUND

Inductively Coupled Plasma (ICP) spectrometry is an analysis technique used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

A device and methods are described that are configured to determine whether a diluted sample is needed and to route the sample to be diluted through a secondary rotary valve from a primary rotary valve. A spectrometry analysis system that employs example techniques in accordance with the present disclosure includes an inline dilution environment, including a first valve assembly configured to prepare a sample by accepting at least one of the sample, a diluent, a carrier, or an internal standard, where the first valve assembly includes a first sample loop; and a second valve assembly configured to prepare the sample by accepting the sample from the first valve assembly, where the second valve assembly is coupled to the first valve assembly, and where the second valve assembly includes a second sample loop. In an implementation, a method includes loading a sample into a first rotary valve having a first sample loop, where loading the sample includes mixing at least one of an internal standard, a diluent, or a carrier to the liquid sample to form a processed sample; isolating the processed sample using a second rotary valve having a second sample loop; and performing multiple injections of the processed sample from the second sample loop into an analyzer without refilling the second loop with another processed sample. In an implementation, a method includes loading a sample into a first sample loop, where loading the sample includes mixing at least one of an internal standard, a diluent, or a carrier to the liquid sample to form a processed sample; dispensing the sample in the first sample loop into a second sample loop; and performing multiple injections of the processed sample from the second sample loop into an analyzer without refilling the second loop with another processed sample.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

DETAILED DESCRIPTION

Overview

Peristaltic pumps and/or rotary piston pumps can be used to dilute an internal standard/spike and/or a sample for analysis with spectrometry equipment. As successive dilutions of an internal standard are supplied (e.g., to create a calibration curve in the case of an internal sample), it becomes necessary to change tubing between each dilution, adding to the time, complexity, and expense associated with calibrating equipment. For example, a test sample can be divided into several test portions. Known quantities of an internal standard may then be added to "spike" one or more of the test portions prior to analysis. Another of the test portions may be analyzed without the internal standard ("unspiked"). This technique can be used to determine the content of an analyte in a test sample, while accounting for the analytical procedure, compensating for matrix effects, and so forth. In this type of test configuration, it is generally desirable that the amount of standard analyte added to a test sample is similar to the amount of analyte already present in the test sample (e.g., in some instances, the amount of standard analyte added to a test sample can range from about one to about five times (1×-5×) the amount of analyte present in the sample). However, if the concentration of analyte in the test sample is not known prior to analysis, it may be necessary to spike a number of test portions with increasing quantities of analyte to create a calibration curve, necessitating a change in tubing between each successive dilution. In some instances, a dilution of 200× or more may be desired, which can be difficult to achieve within the same rotary valve as a non-diluted sample.

With spectrometry equipment, fluid is typically continuously introduced to a nebulizer, which is used to aerosolize the fluid (e.g., using a nebulizer gas, such as Argon). For example, a sample fluid and a carrier fluid may be continuously pumped to a nebulizer, a sample fluid may be intermittently pumped to a nebulizer while a carrier fluid is continuously pumped to a nebulizer, a rinse solution may be pumped to a nebulizer when the sample fluid and the carrier fluid are not being pumped to the nebulizer, and so forth. Continuously pumping fluid to a nebulizer in this manner can lead to increased liquid waste, greater rinse solution consumption, and/or an increased likelihood of flooding a spray chamber connected to a nebulizer (e.g., when an instrument is not being used to analyze samples). Further, this configuration can make it difficult to change-over between solvent systems, if needed, due to the effects of residual fluid in the nebulizer and/or spray chamber from continuous pumping. Additionally, in some instances sequential samples introduced one immediately after another may undesirably chemically react in the aerosol phase (e.g., via acid/base interaction, organic solvent/water interaction, polymerizing chemical interaction, and so forth). This interaction can lead to noise, precipitation, and/or unwanted chemical reactions.

Accordingly, devices and methods are described that are configured to determine whether a diluted sample is needed and to route the sample to be diluted through a secondary rotary valve from a primary rotary valve. A spectrometry analysis system that employs example techniques in accordance with the present disclosure includes an inline dilution environment, including a first valve assembly configured to prepare a sample by accepting at least one of the sample, a diluent, a carrier, or an internal standard, where the first valve assembly includes a first sample loop; and a second valve assembly configured to prepare the sample by accepting the sample from the first valve assembly, where the second valve assembly is coupled to the first valve assembly, and where the second valve assembly includes a second sample loop. In an implementation, a method includes loading a sample into a first rotary valve having a first sample loop, where loading the sample includes mixing at least one of an internal standard, a diluent, or a carrier to the liquid sample to form a processed sample; isolating the processed sample using a second rotary valve having a second sample loop; and performing multiple injections of the processed sample from the second sample loop into an analyzer without refilling the second loop with another processed sample. In an implementation, a method includes loading a sample into a first sample loop, where loading the sample includes mixing at least one of an internal standard, a diluent, or a carrier to the liquid sample to form a processed sample; dispensing the sample in the first sample loop into a second sample loop; and performing multiple injections of the processed sample from the second sample loop into an analyzer without refilling the second loop with another processed sample.

Systems and/or devices configured in accordance with the present disclosure may also include one or more dilution pumps to provide variable online dilution. These systems can be configured to supply an internal standard or a sample using a sample pump, while dilution pumps are controlled to selectively adjust amounts of a carrier and/or a diluent supplied with the internal standard or the sample. Thus, a calibration curve can be created using a single internal standard by varying the ratio of diluent to internal standard using the dilution pumps. Further, the internal standard can be pumped at a constant flow rate for each successive dilution. In implementations, the one or more dilution pumps may also be stopped during time intervals when the sample pump is not pumping sample to a nebulizer.

In implementations where the internal standard or the sample and the carrier are supplied to Inductively Coupled Plasma (ICP) or ICP Mass Spectrometry (ICP-MS) equipment, high dilution flows and carrier flows can be mixed to achieve a steady signal output from the equipment. In example implementations, an internal standard and a sample can be mixed before the addition of a diluent. Mixing the internal standard and the sample before the addition of a diluent can mitigate or prevent a Venturi effect that may otherwise be present when a high diluent flow suctions some of a sample (e.g., at a valve or tee) and creates a fluctuating sample flow that causes a temporary high signal followed by a low signal as the sample flow is recharged at a low flow rate. In one example, when a sample flow rate of two and one half microliters per minute (2.5 μL/min) is used to mix a sample with a diluent at a diluent flow rate of four hundred ninety seven and one half microliters per minute (497.5 μL/min), a first dilution factor (DF1) for the mixture can be two hundred (200) (e.g., (497.5+2.5)/2.5). When the resulting mixture is mixed at a flow rate of five hundred microliters per minute (500 μL/min) with an internal standard at an internal standard flow rate of one hundred fifty microliters per minute (150 μL/min) a second dilution factor (DF2) for the mixture can be one and three tenths (1.3) (e.g., (150+500)/500). However, when the sample is first mixed with the internal standard, the first dilution factor (DF1) can be sixty one (61) (e.g., (150+2.5)/2.5), while the second dilution factor (DF2) can be about four and twenty six one hundredths (4.26) (e.g., (497.5+152.5)/152.5). In additional embodiments, the internal standard or the sample may be supplied using a separate pump from the carrier or the diluent so that it is not necessary to clean the pumps connected to the internal standard, the sample, the carrier, and/or the diluent between each dilution.

The techniques described herein may be implemented in a system that includes a sample pump, a first valve assembly (e.g., primary rotary valve), a second valve assembly (e.g., a secondary rotary valve), and/or one or more dilution pumps to provide variable online dilution. In one or more implementations, the techniques may be implemented as one or more software modules stored in a memory of a device included with the system and executed by a processing system of the device. As described herein, the processing system may execute the module(s) to selectively adjust amounts of a carrier and/or a diluent supplied with an internal standard or a sample. The techniques described herein thus furnish the user of the system with variable online dilution. For example, the system may provide autodilution of a sample and/or an internal standard, linear auto calibration, accurate sample dilution, and so forth. Thus, variable amounts of an internal standard can be mixed with a sample using, for example, a single prepared spike solution. The spike can be diluted automatically using a diluent solution in-line or on-line (e.g., as required by a specified dilution factor). This can result in a savings in labor and materials, provide reliable and precise dilution, allow for a micro standard additions system (e.g., where a required amount of sample is only microliters), provide on-line additions and variable dilution at the same time, and so forth. Allowing for variable dilution and standard addition at the same time may be particularly useful with a viscous solution (e.g., in the case of sulfuric acid, $H_2SO_4$).

In the following discussion, an example device, system environment, and exemplary procedures are described that may be employed with the example environment, as well as with other environments and devices without departing from the spirit and scope thereof.

EXAMPLE IMPLEMENTATIONS

Figure 1:
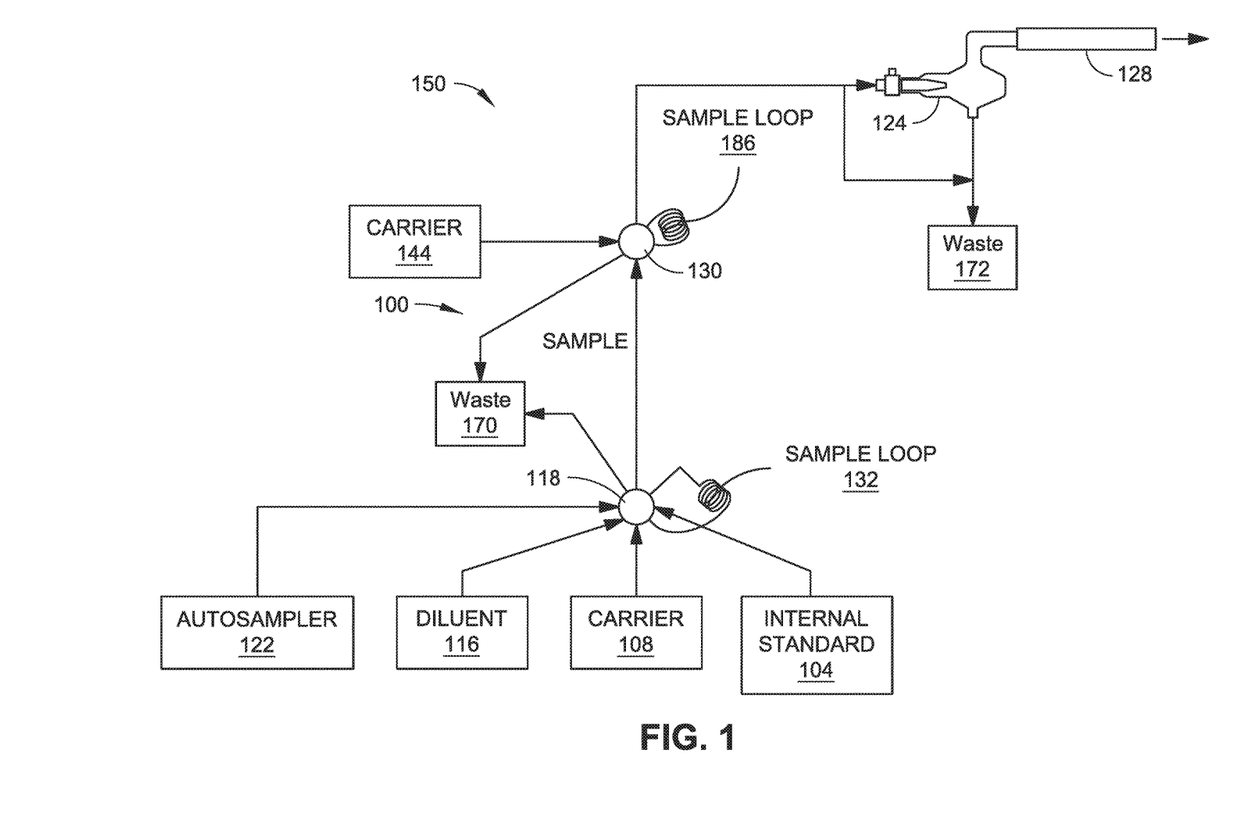
FIG. 1 is a diagrammatic view of an apparatus for performing variable online dilution in accordance with example implementations of the present disclosure.
Figure 2:
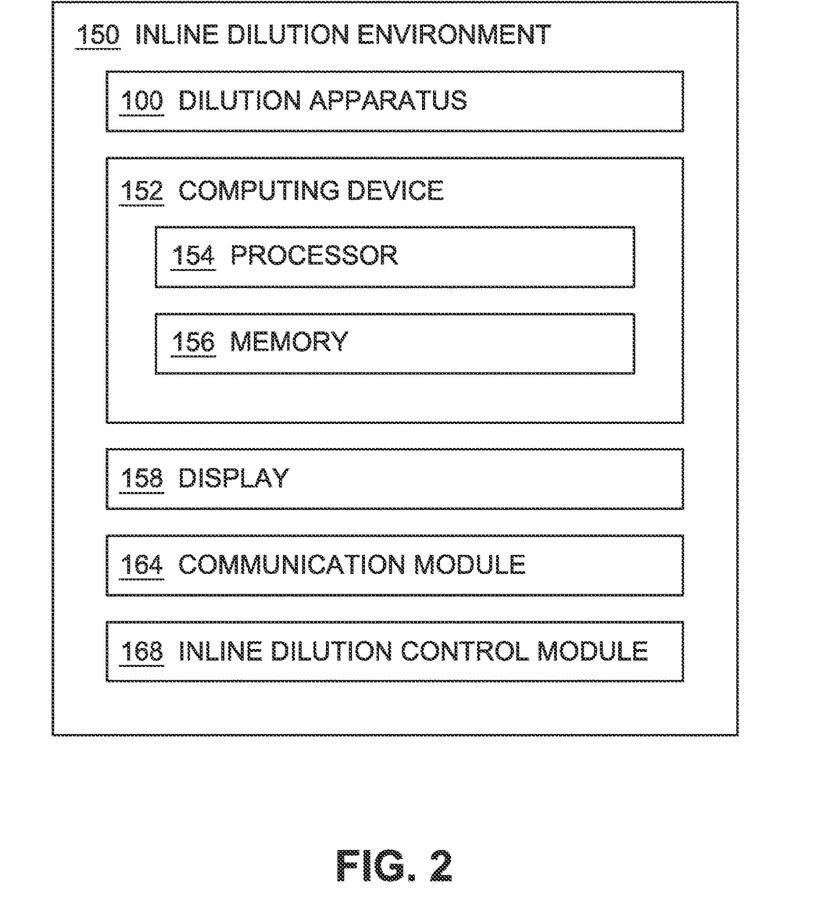
FIG. 2 is a block diagram illustrating an example variable online dilution environment in accordance with example implementations of the present disclosure.

FIGS. 1 and 2 illustrate an exemplary inline dilution apparatus 100 and inline dilution environment 150 that are operable to perform the techniques discussed herein. FIG. 2 illustrates an inline distribution apparatus 100 configured to provide variable online dilution functionality to inline dilution apparatus 100. The inline dilution apparatus 100 may be configured in a variety of ways. For instance, the inline dilution apparatus 100 may include a first valve assembly 118 and a second valve assembly 130, which may include a pump (e.g., a peristaltic pump, a syringe pump) and/or a valve (e.g., a rotary valve). In implementations, the first valve assembly 118 includes inlet lines from a sample source (e.g., autosampler 122), a diluent 116, a carrier 108, and/or an internal standard 104. In one example, a sample is pumped into a first valve assembly 118 and mixed with at least one of an internal standard 104, a diluent 116, and/or a carrier 108 according to a desired dilution rate (e.g., 1× dilution), such that a prepared sample is pumped to a torch assembly 124 at a rate of 200 µL/min. In another example, it is determined that a sample is to be diluted (e.g., 200× dilution). In this example, a sample is pumped into a first valve assembly 118 and mixed with a carrier 108, a diluent 116, and/or an internal standard 104. Further in this example, the sample is then pumped from the first valve assembly 118 to a second valve assembly 130, mixed with a carrier 144 (e.g., at a rate of 20,000 µL/min), and pumped to a torch assembly 124 (e.g., at a rate of 200 µL/min). Any excess diluted sample not pumped to the torch assembly 124 may be pumped to a waste outlet. In this way, a sample may be diluted (e.g., up to 200× dilution) using the same inline dilution environment 150. The inline dilution environment 150 may include other pumps, such as an internal standard syringe pump. Further disclosed below, an inline dilution environment 150 can include a dilution apparatus 100, a computing device 152, a display 158, a communication module 164, and/or an inline dilution control module 168. In implementations, the first valve assembly 118 and/or the second valve assembly can function to serve as an isolation valve for the processed sample.

In implementations, the inline dilution apparatus 100 can be configured to supply a sample (e.g., a liquid, carrier, diluent, rinse solution and so forth) to an analyzer 128 and/or a torch assembly 124, which may include a nebulizer, a plasma torch, etc. It should be noted that "sample" within the context of the present disclosure may refer to sample fluid for analysis (e.g., by spectrometry equipment), a carrier 108, 144, and/or diluent 116 to be combined with sample, and/or rinse solution. Thus, a carrier 108, 144 may be used with a liquid sample during a first time interval and the supply of carrier and sample may be stopped subsequent to the first time interval, such that substantially no liquid is supplied to the torch assembly 124 during a second time interval subsequent to the first time interval. Then, a rinse solution may be supplied to the torch assembly 124 during a third time interval subsequent to the second time interval.

The inline dilution device 100 including the first valve assembly 118 and the second valve assembly 130 may be included in a single hardware module (e.g., provided with a unitary housing). For example, output lines of an internal standard syringe pump and/or a diluent syringe pump may be directly connected to the first valve assembly 118, while output lines of a carrier syringe pump and possibly a diluent syringe pump may be connected together, and the resulting output may be connected to the first valve assembly 118. However, an example having a hardware module is provided by way of example only and is not meant to be restrictive of the present disclosure. Thus, it will be appreciated that other hardware modules having different configurations may be provided in accordance with the present disclosure.

The internal standard pump 104 is configured to pump an internal standard 104 in a specified time interval, and the carrier syringe pump(s) and/or the diluent pump 116 are configured to pump volumes of the carrier 108 and/or the diluent 116 in the specified time interval. In some implementations, a second carrier pump can be configured to pump another volume of the carrier 108 within the dilution apparatus 100 in the specified time interval. Similarly, a third pump can be configured to pump a further volume of the carrier 108 within the dilution apparatus 100 in the specified time interval. In this manner, various dilutions of the internal standard 104 and/or a sample can be furnished online by controlling amounts of the carrier 108 and/or the diluent 116 that are supplied by the first carrier pump, the second carrier pump, the third carrier pump, the diluent pump, and/or additional syringe pumps, while pumping the internal standard 104 and/or a sample during a specified time interval. Additionally, the different pumps can pump at different rates to create the desired dilutions.

In an implementation, a sample supplied at a flow rate of two hundred microliters per minute (200 µL/min) can be mixed with a diluent 116 and/or a mixture of a spike and a spike diluent supplied at a flow rate of one hundred fifty microliters per minute (150 µL/min). The spike can be supplied using, for example, a three hundred microliter (300 µL) syringe, while the spike diluent can be supplied using, for example, a three thousand microliter (3,000 µL) syringe.

In a first embodiment, a spike diluent can be supplied at a flow rate of one hundred fifty microliters per minute (150 µL/min). In a second embodiment, the spike diluent can be supplied at a flow rate of one hundred and forty microliters per minute (140 µL/min) and the spike can be supplied at a flow rate of ten microliters per minute (10 µL/min). In a third embodiment, the spike diluent can be supplied at a flow rate of one hundred thirty microliters per minute (130 µL/min) and the spike can be supplied at a flow rate of twenty microliters per minute (20 µL/min). In a fourth embodiment, the spike diluent can be supplied at a flow rate of one hundred microliters per minute (100 µL/min) and the spike can be supplied at a flow rate of fifty microliters per minute (50 µL/min). The total flow rate in each of these specific instances is four hundred microliters per minute (400 µL/min) and the dilution factors are about one (1), one and seventy one thousandths (1.071), one and one hundred fifty four thousandths (1.154), and one and a half (1.5), respectively.

The inline dilution apparatus 100 may include a sampler assembly, such as an autosampler 122, for automatically collecting a sample from a number of prepared samples contained in test tubes, and so forth. The inline dilution apparatus 100 may also include a torch assembly 124 (e.g., may be coupled with a cyclonic spray chamber) for supplying an analyzer 128 (e.g., Inductively Coupled Plasma (ICP) torch) with sample gas, samples from the autosampler 122, the internal standard 104, the carrier 108, and/or the diluent 116. A second valve assembly 130 may be coupled with the first valve assembly 118, and/or the torch assembly 124, for example, of a hardware module. The first valve assembly 118 may receive samples from the autosampler 122, the internal standard 104, the carrier 108, and/or the diluent 116 and supply them to the torch assembly 124 and/or the second valve assembly 130. The first valve assembly 118 and/or the second valve assembly 130 may also be coupled with a sample loop 132, 186 for holding priming fluid and so forth. A peristaltic pump may be used to evacuate waste from the torch assembly 124 or the first valve assembly 118 and/or second valve assembly 130. For example, the peristaltic pump may be fluidly coupled to a drain chamber of the torch assembly 124.

FIG. 2 illustrates an exemplary a dilution environment 150 including a computing device 152 with the computing device 152 including a processor 154 and a memory 156. The processor 154 provides processing functionality for the computing device 152 and may include any number of processors, micro-controllers, or other processing systems, and resident or external memory for storing data and other information accessed or generated by the computing device 152. The processor 154 may execute one or more software programs that implement the techniques and modules described herein. The processor 154 is not limited by the materials from which it is formed or the processing mechanisms employed therein and, as such, may be implemented via semiconductor(s) and/or transistors (e.g., electronic integrated circuits (ICs)), and so forth.

The memory 156 may include device-readable storage media that provides storage functionality to store various data associated with the operation of the computing device 152, such as a software program and/or code segments, or other data to instruct the processor 154 and other elements of the computing device 152 to perform the techniques described herein. A wide variety of types and combinations of memory 156 may be employed. The memory 156 may be integral with the processor 154, stand-alone memory, or a combination of both. The memory may include, for example, removable and non-removable memory elements such as RAM, ROM, Flash (e.g., SD Card, mini-SD card, micro-SD Card), magnetic, optical, USB memory devices, and so forth. In embodiments of the computing device 152, the memory 156 may include removable ICC (Integrated Circuit Card) memory such as provided by SIM (Subscriber Identity Module) cards, USIM (Universal Subscriber Identity Module) cards, UICC (Universal Integrated Circuit Cards), and so on.

The computing device 152 may include a display 158 to display information to a user of the computing device 152. In some embodiments, the display 158 may comprise a CRT (Cathode Ray Tube) display, an LED (Light Emitting Diode) display, an OLED (Organic LED) display, an LCD (Liquid Crystal Diode) display, a TFT (Thin Film Transistor) LCD display, an LEP (Light Emitting Polymer) or PLED (Polymer Light Emitting Diode) display, and so forth, configured to display text and/or graphical information such as a graphical user interface. The display 158 may be backlit via a backlight such that it may be viewed in the dark or other low-light environments.

The display 158 may be provided with and/or include a touch screen configuration to receive input (e.g., data, commands, etc.) from a user. For example, a user may operate the computing device 152 by touching the touch screen and/or by performing gestures on the touch screen. In some embodiments, the touch screen may be a capacitive touch screen, a resistive touch screen, an infrared touch screen, combinations thereof, and the like. The computing device 152 may further include one or more input/output (I/O) devices (e.g., a keypad, buttons, a wireless input device, a thumbwheel input device, a trackstick input device, and so on). The I/O devices may include one or more audio I/O devices, such as a microphone, speakers, and so on.

The computing device 152 may also include a communication module 164 representative of communication functionality to permit computing device 152 to send/receive data between different devices (e.g., components/peripherals) and/or over one or more networks. Communication module 164 may be representative of a variety of communication components and functionality including, but not necessarily limited to: a browser; a transmitter and/or receiver; data ports; software interfaces and drivers; networking interfaces; data processing components; and so forth.

The one or more networks are representative of a variety of different communication pathways and network connections which may be employed, individually or in combinations, to communicate among the components of the inline dilution environment 150. Thus, the one or more networks may be representative of communication pathways achieved using a single network or multiple networks. Further, the one or more networks are representative of a variety of different types of networks and connections that are contemplated including, but not necessarily limited to: the Internet; an intranet; a Personal Area Network (PAN); a Local Area Network (LAN) (e.g., Ethernet); a Wide Area Network (WAN); a satellite network; a cellular network; a mobile data network; wired and/or wireless connections; and so forth.

Inline dilution control module 168 may comprise software, which is storable in memory 156 and executable by the processor 154, to perform a specific operation or group of operations to furnish functionality to the computing device 152. The inline dilution control module 168 provides functionality to control the dilution of the internal standard 104 and/or the samples from a sample source, such as the autosampler 122. For example, the inline dilution control module 168 may control amounts of the carrier 108 and/or the diluent 116 that are supplied by a carrier pump, a diluent pump, and/or other pumps, while pumping the internal standard 104 and/or a sample during a specified time interval.

In implementations, the inline dilution control module 168 can include a user interface with a browser (e.g., for implementing functionality of the inline dilution control module 168). The browser can enable the computing device 152 to display and interact with content such as a webpage within the World Wide Web, a webpage provided by a web server in a private network, and so forth. The browser may be configured in a variety of ways. For example, the browser may be configured as a portion of the inline dilution control module 168 accessed by the user interface. The browser may be a web browser suitable for use by a full resource device with substantial memory and processor resources (e.g., a smart phone, a personal digital assistant (PDA), etc.).

Generally, any of the functions described herein can be implemented using software, firmware, hardware (e.g., fixed logic circuitry), manual processing, or a combination of these implementations. The terms "module" and "functionality" as used herein generally represent software, firmware, hardware, or a combination thereof. The communication between modules in the inline dilution environment 150 of FIG. 2, for example, can be wired, wireless, or some combination thereof. In the case of a software implementation, for instance, a module may represent executable instructions that perform specified tasks when executed on a processor, such as the processor 154. The program code can be stored in one or more device-readable storage media, an example of which is the memory 156 associated with the computing device 152 of FIG. 2.

Example Procedures

The following discussion describes procedures that may be implemented by an inline dilution apparatus 100 providing variable online dilution functionality. Aspects of the procedures may be implemented in hardware, firmware, or software, or a combination thereof. The procedures are represented by a set of blocks that specify operations performed by one or more devices and are not necessarily limited to the orders shown for performing the operations by the respective blocks. In portions of the following discussion, reference may be made to the inline dilution apparatus 100 and the inline dilution environment 150 of FIGS. 1 and 2. The features of techniques described below are platform-independent, meaning that the techniques may be implemented on a variety of commercial platforms having a variety of processors.

Figure 3:
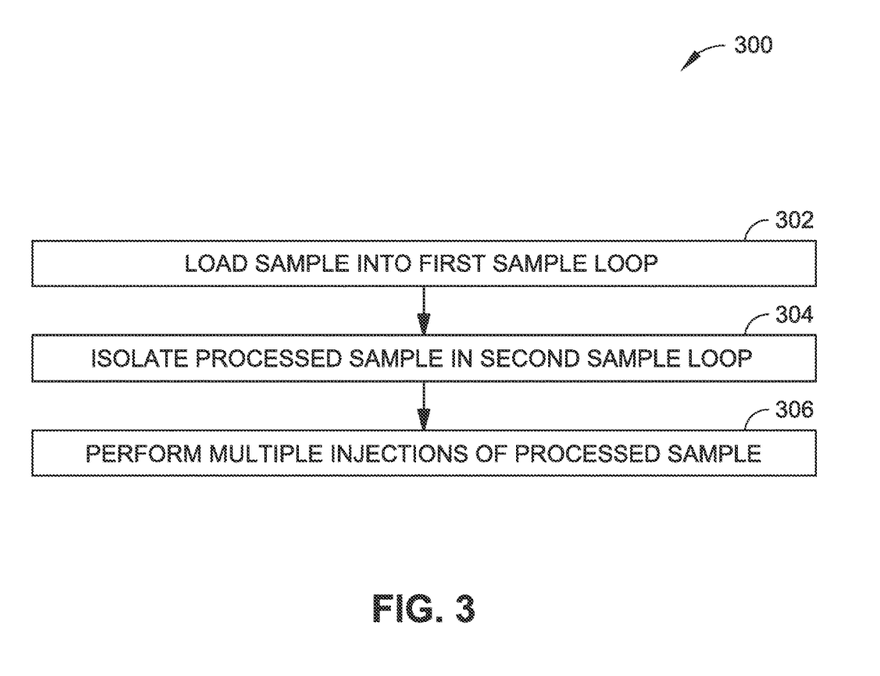
FIG. 3 is a flow diagram illustrating a method for performing variable online dilution in accordance with example implementations of the present disclosure.

FIG. 3 depicts a procedure 300 in an example implementation in which variable inline dilution is provided using an inline dilution apparatus 100 and/or an inline dilution environment 150. As shown in FIG. 3, a sample is loaded into a first sample loop from a sample source (Block 302). The sample can be processed in the first sample loop 132 by adding at least one of a diluent 116, a carrier 108, and/or an internal standard 104. Then, the processed sample is transferred to and isolated in a second sample loop (Block 304). The processed sample is isolated from the first sample loop such that another sample can be loaded into a first sample loop 132 without contaminating the processed sample in the second sample loop 186. In another implementation, isolating a processed sample in the second sample loop 186 can include diluting the sample, which results in a processed sample. For example, as shown in FIGS. 1 and 2, the processor 154 may be configured to determine a specified dilution for an internal standard 104 and/or a sample from the autosampler 122 and selectively adjust the volume of carrier 108 pumped in a specified time interval to furnish the specified dilution for the internal standard 104 and/or the sample. In a specific example, the inline dilution control module 168 may include control programming used to calculate one or more dilutions for a sample and/or an internal standard. Additionally, an operator may provide a desired dilution and/or a range of desired dilutions via a data entry device, such as a keyboard, a touchpad, and so forth.

In an implementation, isolating a processed sample can include adding a diluent 116, a carrier 108, or an internal standard 104 to the sample using at least one of a primary rotary pump 118 or the secondary rotary pump 130. For example, with continuing reference to FIGS. 1 and 2, the processor 154 may execute the control programming to control the pumping rates of the autosampler 122, an internal standard syringe pump, a carrier syringe pump, and/or a diluent syringe pump to furnish the specified dilution for the internal standard 104 and/or sample.

When the internal standard 104 is pumped at a constant flow rate, for example, the processor 154 may be configured to selectively adjust volumes of carrier 108 pumped by the carrier pump in a specified time interval to furnish the specified dilution for the internal standard 104 with respect to the carrier 108. In a specific instance, the control programming may include a threshold selected to control a switchover between multiple pumps.

Next, the processed sample is injected into an analyzer (Block 306). In an implementation, the inline dilution apparatus 100 can inject the processed sample from the second sample loop into the analyzer 128 and/or torch assembly 124 for variable periods of time, which can also include fixed replicates (e.g. 3×0.1 s injections+3×0.5 s injections+3×1 s injections, etc.) to introduce the processed sample to the analyzer 128. The processed sample may be repeatedly (e.g., multiple injections) introduced from a single loop (e.g., the second sample loop 130) without reloading the single loop to gather statistical information on the processed sample.

Figure 4:
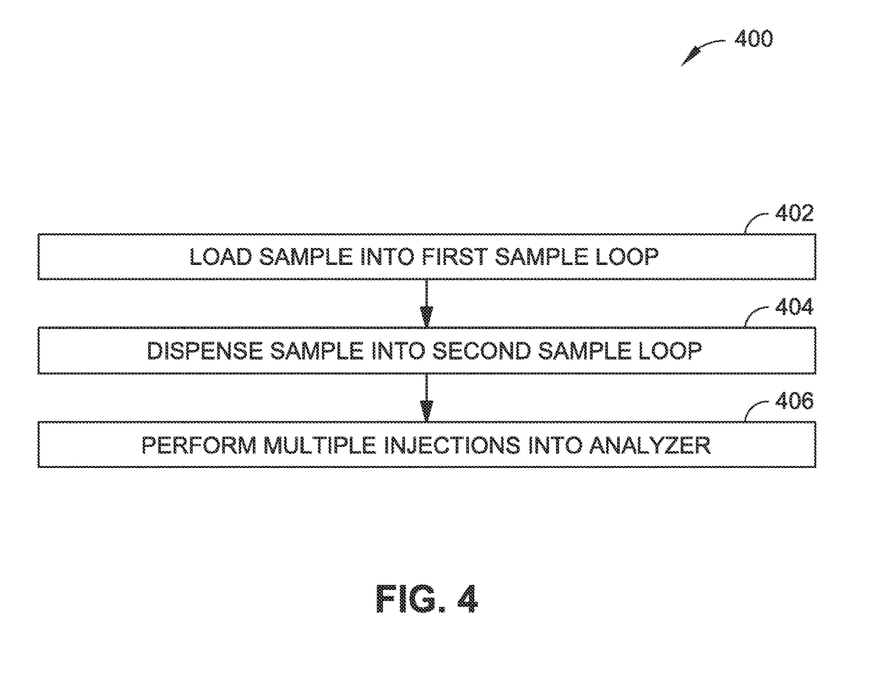
FIG. 4 is a flow diagram illustrating a method for performing variable online dilution in accordance with example implementations of the present disclosure.
Figure 5A:
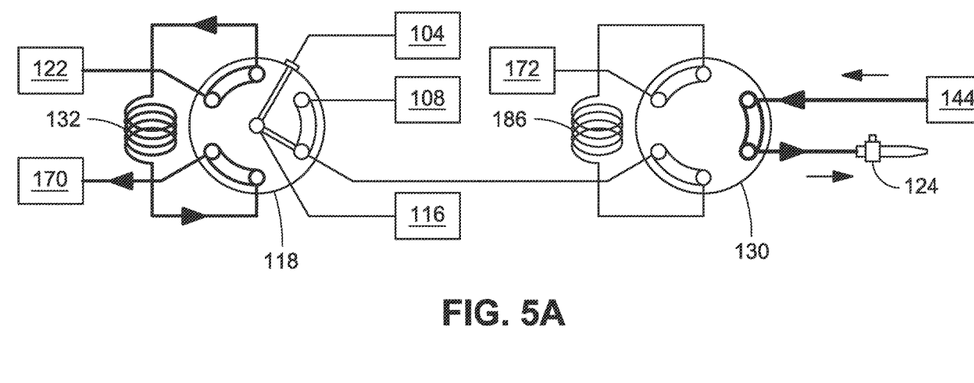
FIG. 5A is a diagrammatic view illustrating steps for performing sample dilution prior to dilution and/or using an apparatus, such as the spectrometry analysis system shown in FIGS. 1 and 2, in accordance with the process shown in FIGS. 3 and 4.
Figure 5B:
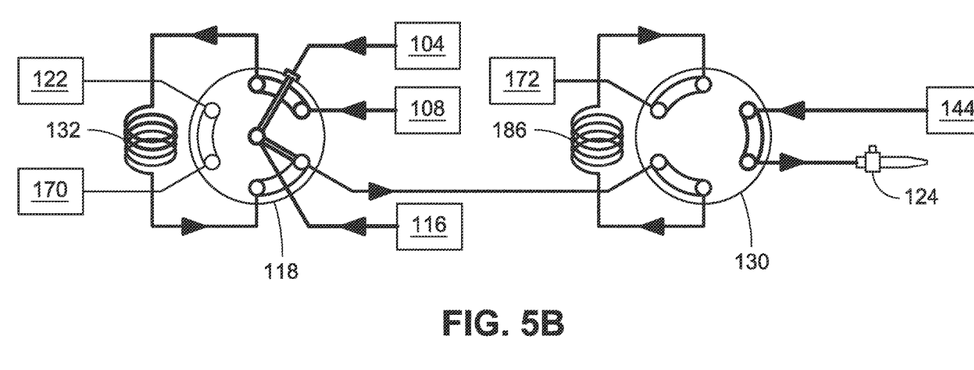
FIG. 5B is a diagrammatic view illustrating steps for performing sample dilution prior to dilution and/or using an apparatus, such as the spectrometry analysis system shown in FIGS. 1 and 2, in accordance with the process shown in FIGS. 3 and 4.
Figure 5C:
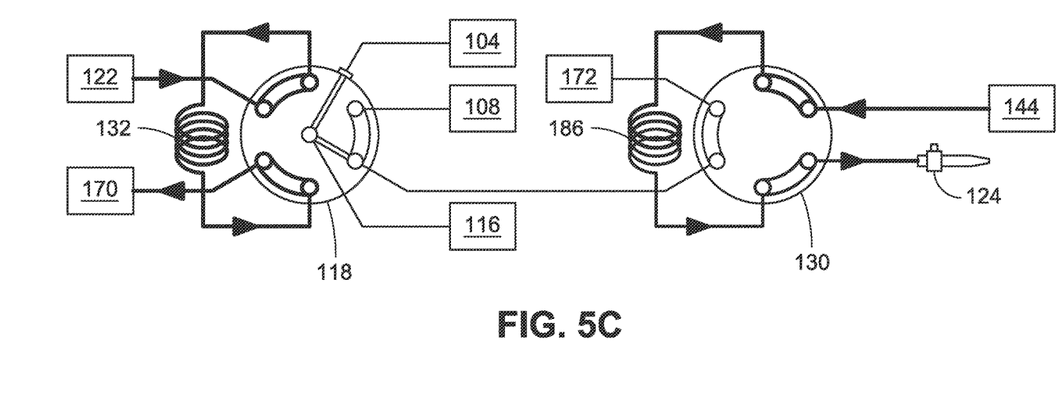
FIG. 5C is a diagrammatic view illustrating steps for performing sample dilution prior to dilution and/or using an apparatus, such as the spectrometry analysis system shown in FIGS. 1 and 2, in accordance with the process shown in FIGS. 3 and 4.
Figure 5D:
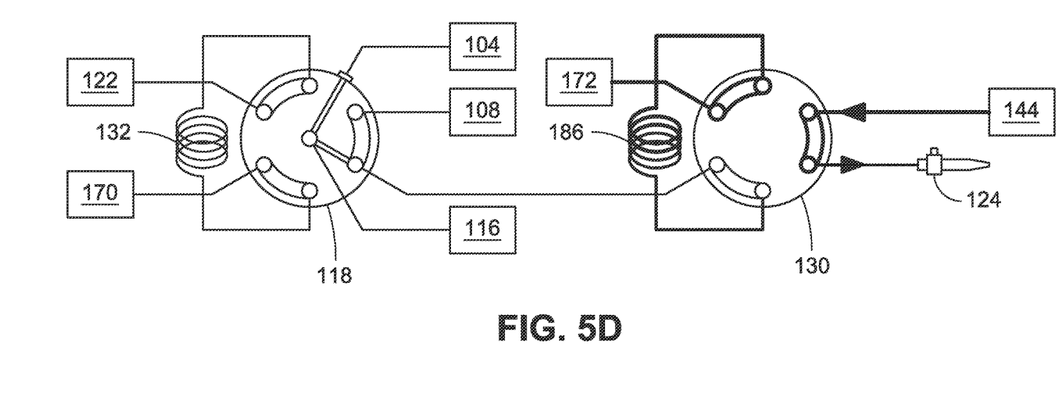
FIG. 5D is a diagrammatic view illustrating steps for performing sample dilution prior to dilution and/or using an apparatus, such as the spectrometry analysis system shown in FIGS. 1 and 2, in accordance with the process shown in FIGS. 3 and 4.
Figure 5E:
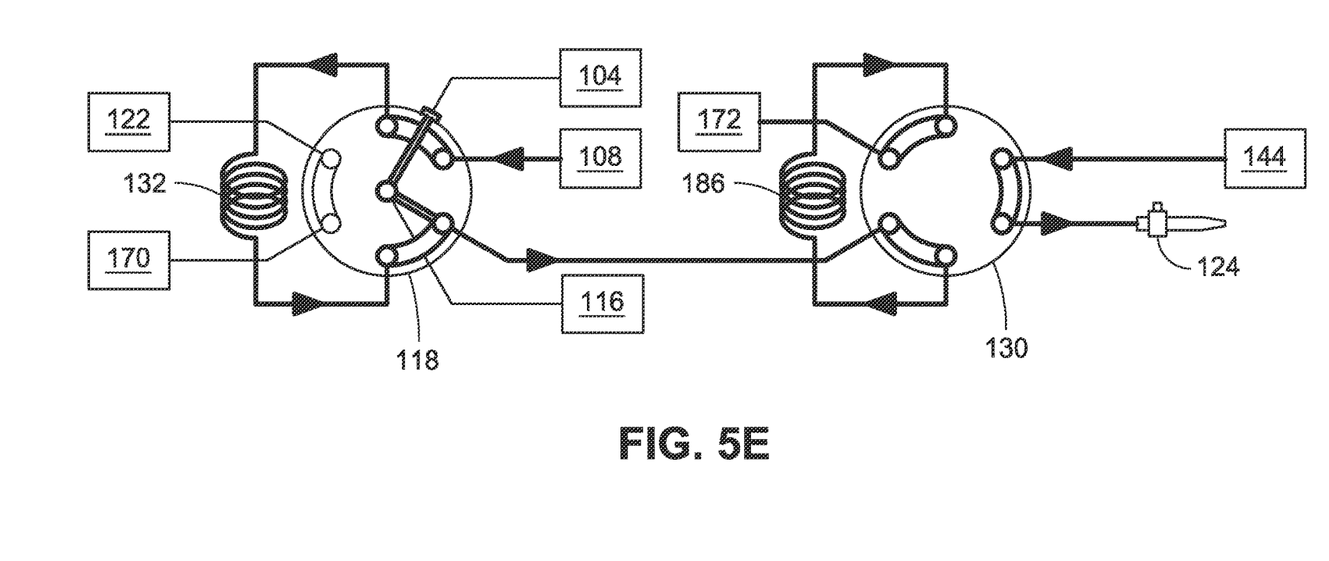
FIG. 5E is a diagrammatic view illustrating steps for performing sample dilution prior to dilution and/or using an apparatus, such as the spectrometry analysis system shown in FIGS. 1 and 2, in accordance with the process shown in FIGS. 3 and 4.

FIG. 4 through FIG. 5E depict a procedure 400 in an example implementation in which variable inline dilution is provided with an inline dilution apparatus 100 and inline dilution environment 150. In FIGS. 5A through 5E, the bold lines depicts the active path of the sample and processed sample. As shown in FIG. 4 and FIG. 5A, a sample is received from a sample source and loaded into a first sample loop (Block 402). Receiving the sample and loading the sample can include receiving the sample from an autosampler 122.

As shown in FIG. 4 and FIG. 5B, the sample is then dispensed into a second sample loop (Block 404). Dispensing the sample into the second sample loop can include adding at least one of a diluent 116, a carrier 108, and/or an internal standard 104. Dispensing the sample to the second sample loop 186 can include isolating the processed sample from the first sample loop 132 such that another sample can be loaded into the first sample loop 132, as shown in FIG. 5C.

Next, the processed sample is injected into an analyzer (Block 406). In an implementation shown in FIG. 5D, the inline dilution apparatus 100 can inject the processed sample from the second sample loop into the analyzer 128 and/or torch assembly 124 for variable periods of time, which can also include fixed replicates (e.g. 3×0.1 s injections+3×0.5 s injections+3×1 s injections, etc.) to introduce the processed sample to the analyzer 128. The processed sample may be repeatedly (e.g., multiple injections) introduced from a single loop (e.g., the second sample loop 130) without reloading the single loop to gather statistical information on the processed sample. Subsequent to analysis of a processed sample and/or prior to loading any sample, the inline dilution environment 154 and/or inline dilution apparatus 100 can be cleaned and/or flushed, as shown in FIG. 5E.

In some implementations, the control programming may be used to identify each particular dilution from a single vial of a sample supplied from the autosampler 122 as one of multiple different sample vials when interfacing with, for example, data analysis software. Thus, multiple virtual vial locations may be generated using a single physical vial location.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A spectrometry analysis system including an inline dilution environment, comprising:
    a dilution apparatus including
        a first valve assembly configured to prepare a first sample by accepting at least one of the first sample, a diluent, a carrier, or an internal standard, where the first valve assembly includes a first sample loop within the first valve assembly, and where the first sample loop prepares the first sample within the first valve assembly;
        a second valve assembly configured to prepare the first sample by accepting the first sample from the first valve assembly, where the second valve assembly is coupled to the first valve assembly, where the second valve assembly includes a second sample loop within the second valve assembly, where the second sample loop isolates the first sample for injection into a torch assembly, and where the first valve assembly accepts and prepares a second sample while the first sample is isolated in the second sample loop; and
        the torch assembly coupled to the dilution apparatus, where the second sample loop isolates and dilutes the first sample for injection into a torch assembly, and where the second valve assembly is coupled with the first valve assembly and the torch assembly;
    wherein the dilution apparatus is configured to perform multiple injections of the prepared first sample to an analysis device.

2. The spectrometry analysis system in claim 1, wherein at least one of the first valve assembly or the second valve assembly includes a rotary valve.

3. The spectrometry analysis system of claim 1, further comprising:
    an analysis device coupled to the second rotary valve and configured to receive a processed sample from the second rotary valve and the second sample loop.

4. The spectrometry analysis system in claim 3, wherein the analysis device includes an inductively coupled plasma mass spectrometer (ICPMS).

5. A method for analyzing a liquid sample, comprising:
    loading a sample into a first rotary valve having a first sample loop, where loading the sample includes mixing at least one of an internal standard, a diluent, or a carrier to the liquid sample to form a processed sample, where the first sample loop prepares the processed sample within the first rotary valve;
    isolating the processed sample using a second rotary valve having a second sample loop, where the second sample loop isolates the processed sample within the second rotary valve for injection into a torch assembly while the first sample loop accepts and prepares a second sample; and
    performing multiple injections of the processed sample from the second sample loop into an analyzer without refilling the second loop with another processed sample, where the analyzer includes a torch assembly, wherein the second rotary valve is coupled with the first rotary valve and the torch assembly.

6. The method for analyzing a liquid sample of claim 5, where dispensing the liquid sample in the first sample loop into a second sample loop includes isolating the processed sample using at least one isolation valve.

7. The method for analyzing a liquid sample of claim 5, where dispensing the liquid sample in the first sample loop into a second sample loop includes diluting the sample in the second sample loop to form the processed sample.

8. The method for analyzing a liquid sample of claim 5, where dispensing the liquid sample in the first sample loop into a second sample loop includes mixing the sample with at least one of a diluent or an internal standard in the second sample loop.

9. The method for analyzing a liquid sample of claim 5, where performing multiple injections of the processed sample from the second sample loop into an analyzer includes injecting the processed sample into a nebulizer on an inductively-coupled plasma mass spectrometer.

10. The method for analyzing a liquid sample of claim 5, where performing multiple injections of the processed sample from the second sample loop into an analyzer includes injecting a constant volume for each of the multiple injections.

11. A method for analyzing a liquid sample, comprising:
    loading a sample into a first sample loop, where loading the sample includes mixing at least one of an internal standard, a diluent, or a carrier to the liquid sample to form a processed sample, where the first sample loop prepares the processed sample within a first valve assembly;
    dispensing the sample in the first sample loop into a second sample loop, where the second sample loop isolates the processed sample within a second valve assembly for injection into a torch assembly; and
    performing multiple injections of the processed sample from the second sample loop into an analyzer without refilling the second loop with another processed sample while the first sample loop accepts and prepares a second sample, where the analyzer includes a torch assembly, wherein the second rotary valve is coupled with the first rotary valve and the torch assembly.

12. The method for analyzing a liquid sample of claim 11, where dispensing the liquid sample in the first sample loop into a second sample loop includes isolating the processed sample using at least one isolation valve.

13. The method for analyzing a liquid sample of claim 11, where dispensing the liquid sample in the first sample loop into a second sample loop includes diluting the sample in the second sample loop to form the processed sample.

14. The method for analyzing a liquid sample of claim 11, where dispensing the liquid sample in the first sample loop into a second sample loop includes mixing the sample with at least one of a diluent or an internal standard in the second sample loop.

15. The method for analyzing a liquid sample of claim 11, where performing multiple injections of the processed sample from the second sample loop into an analyzer includes injecting the processed sample into a nebulizer on an inductively-coupled plasma mass spectrometer.

16. The method for analyzing a liquid sample of claim 11, where performing multiple injections of the processed sample from the second sample loop into an analyzer includes injecting a constant volume for each of the multiple injections.

17. The method for analyzing a liquid sample of claim 11, where performing multiple injections of the processed sample from the second sample loop into an analyzer includes controlling the injection volume using timing.

18. The method for analyzing a liquid sample of claim 11, where performing multiple injections of the processed sample from the second sample loop into an analyzer includes a transient signal produced at the analyzer by the injection time.

* * * * *